United States Patent [19]

Demerson et al.

[11] 4,226,860
[45] Oct. 7, 1980

[54] SPIROINDOLONES

[75] Inventors: Christopher A. Demerson, Montreal; Leslie G. Humber, Dollard des Ormeaux, both of Canada

[73] Assignee: American Home Products Corporation, New York, N.Y.

[21] Appl. No.: 64,342

[22] Filed: Aug. 6, 1979

[51] Int. Cl.$^2$ .................. A61K 31/405; A61K 31/54; C07D 209/96; C07D 493/10
[52] U.S. Cl. ............................... 424/240; 260/325 R; 424/246; 424/250; 424/263; 424/267; 424/274
[58] Field of Search .................... 260/325 R; 424/274, 424/246, 240, 250, 267

[56] References Cited

U.S. PATENT DOCUMENTS 3,308,134 3/1967 Plostnieks .................. 260/325 R
3,723,459 3/1973 Paragamian .................. 260/325 R

OTHER PUBLICATIONS

Jönsson et al., Acta Chem. Scand., B, vol. 28, pp. 225–232, (1974).
Patrick et al., J. Am. Chem. Soc., vol. 72, pp. 633–634, (1950).
Witkop et al., J. Am. Chem. Soc., vol. 75, pp. 2572–2576, (1953).
Sundberg, The Chemistry of Indoles, (Academic Press, New York, 1970), pp. 296–303.

*Primary Examiner*—Alton D. Rollins
*Attorney, Agent, or Firm*—Arthur E. Wilfond

[57] ABSTRACT

Herein is disclosed spiroindolone derivatives of the formula

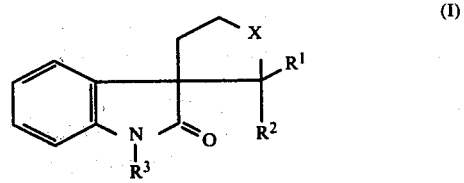

(I)

in which $R^1$ is lower alkyl or carboxy(lower)alkyl, $R^2$ is lower alkyl, $R^3$ is lower alkyl or phenyl(lower)alkyl, and X is oxygen or $CH_2$, or a therapeutically acceptable base addition salt thereof when $R^1$ is carboxy(lower)alkyl, a process for their preparation, methods of using the derivatives and pharmaceutical compositions of the derivatives. The derivatives are useful for treating hypertension in a mammal.

16 Claims, No Drawings

SPIROINDOLONES

BACKGROUND OF THE INVENTION (a) Field of the Invention

This invention relates to novel spiroindolone derivatives. More specifically, this invention relates to spiro[cyclopentane-1,3′[3H]-indole]-2′-one derivatives, and to spiro[furan-3(2H),3′(3H)-indol]-2′-one derivatives and their thia analogs, to a process for their preparation, to methods of using the derivatives and to pharmaceutical compositions of the derivatives. These derivatives are useful for treating hypertension in mammals.

(b) Description of the Prior Art

The closest prior art of which applicants are aware is the spiro[cyclopentane-1,3′-[3H]-indol]-2′(1′H)-ones as exemplified by B. Witkop and J. B. Patrick, J. Amer. Chem. Soc., 75, 2572 (1953) having a spiro ring at position 3 of the indol-2-one. However, the prior art compounds lack the substituents on the spirocyclopentane ring, which are characteristic of the compounds of this invention.

SUMMARY OF THE INVENTION

The compounds of this invention are represented by formula I

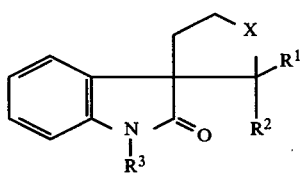

(I)

in which $R^1$ is lower alkyl or carboxy(lower)alkyl, $R^2$ is lower alkyl, $R^3$ is lower alkyl or phenyl(lower)alkyl, and X is oxygen or $CH_2$, or a therapeutically acceptable base addition salt thereof when $R^1$ is carboxy(lower)alkyl.

A preferred group of compounds of formula I are those in which $R^1$ is lower alkyl or carboxymethyl, $R^2$ is lower alkyl, $R^3$ is lower alkyl or phenylmethyl, and X is oxygen or $CH_2$, or a therapeutically acceptable base addition salt thereof when $R^1$ is carboxymethyl.

A pharmaceutical composition is provided by combining the compound of formula I, or a therapeutically acceptable base addition salt thereof when $R^1$ is carboxy(lower)alkyl, and a pharmaceutically acceptable carrier.

The compounds of this invention can be used to treat hypertension in a hypertensive mammal by administering to the mammal an effective antihypertensive amount of a compound of formula I or a therapeutically acceptable base addition salt thereof when $R^1$ is carboxy(lower)alkyl.

The compounds of formula I are prepared by oxidizing a compound of formula II

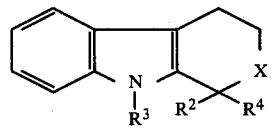

(II)

in which $R^2$, $R^3$ and X are as defined herein and $R^4$ is lower alkyl or lower alkoxycarbonyl(lower)alkyl with sodium periodate to obtain, in the instance wherein $R^4$ of the compound of formula II is lower alkyl, the corresponding compound of formula I in which $R^1$ is lower alkyl, and $R^2$, $R^3$ and X are as defined herein, or in the instance wherein $R^4$ of the compound of formula II is lower alkoxycarbonyl(lower)alkyl, the corresponding compound of formula III

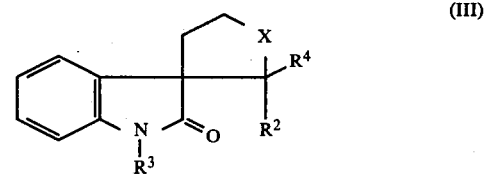

(III)

in which $R^2$, $R^3$ and X are as defined herein and $R^4$ is lower alkoxycarbonyl(lower)-alkyl, and hydrolyzing the compound of formula III under alkaline conditions to obtain the corresponding compound of formula I in which $R^1$ is carboxy(lower)-alkyl, and $R^2$, $R^3$ and X are as defined herein.

DETAILED DESCRIPTION OF THE INVENTION

The term "lower alkyl" as used herein, either alone or as part of a compound word, means straight chain alkyl radicals containing from one to six carbon atoms, and includes methyl, ethyl, propyl, butyl, pentyl and hexyl, and branched chain alkyl radicals containing three or four carbon atoms, and includes isopropyl, isobutyl and tert butyl.

The term "lower alkoxy", as used herein as part of the larger term "lower alkoxycarbonyl(lower)alkyl", means straight chain alkoxy radicals containing one to six carbon atoms and includes methoxy, ethoxy, propoxy, butoxy and hexanoxy and branched alkoxy radicals containing three and four carbon atoms and includes isopropoxy, isobutoxy and tert butoxy.

The term "lower alkanol" as used herein means both straight and branched chain alkanols containing from one to four carbon atoms and includes methanol, ethanol, isopropanol, butanol and the like.

The term "therapeutically acceptable base addition salt" as used herein also includes the therapeutically acceptable inorganic or organic base addition salts of the compound of formula I in which $R^1$ is carboxy(lower)alkyl, i.e. compounds of formula I which are acids. These derived salts possess the same activity as the parent acid and are included within the scope of this invention. The acid is transformed in excellent yield into the corresponding therapeutically acceptable salt by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines: lower mono-, di- and trialkylamines, the alkyl radicals of which contain up to three carbon atoms, such as methylamine, dimethylamine, trimethylamine, ethylamine, di- and tri-ethylamine, N-methyl-N-ethylamine, and the like; mono-, di- and trialkanolamines, the alkanol radicals of which contain up to three carbon atoms, for example, mono-, di- and triethanolamine;

alkylene-diamines which contain up to six carbon atoms, such as hexamethylenediamine; phenylalkylamines, for example, benzylamine, phenylethylamine and N-methylphenylethylamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)-piperidine, as well as pyridine. Furthermore, there may be mentioned the corresponding quaternary salts, such as the tetraalkyl (for example tetramethyl), alkyl-alkanol (for example methyltriethanol and trimethyl-monoethanol) and cyclic ammonium salts, for example the N-methylpyridinium, N-methyl-N-(2-hydroxyethyl)-morpholinium, N,N-dimethylmorpholinium, N-methyl-N-(2-hydroxyethyl)-morpholinium, N,N-dimethylpiperidinium salts, which are characterized by having good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula I in water containing at least one equivalent amount of a hydroxide, carbonate, or bicarbonate corresponding to the inorganic salt desired. Advantageously, the reaction is performed in a water-miscible, inert organic solvent, for example, methanol, ethanol, dioxane, and the like, in the presence of water. For example, such use of sodium hydroxide sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acidic compound of formula I is dissolved in a suitable solvent of either moderate or lower polarity, for example, ethanol, methanol, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula I with an equivalent amount of the corresponding quaternary ammonium hydroxide in water solution, followed by evaporation of the water.

Also included in this invention are the stereochemical isomers of the compounds of formula I which result from asymmetric centers, contained therein. Such stereochemicals are obtained in substantially pure form by classical separation techniques and by sterically controlled synthesis.

Individual enantiomers, which might be separated by fractional crystallization of the diastereomeric salts thereof, are also included.

The antihypertensive effect of the compounds of formula I is demonstrated in standard pharmacological tests, for example, in tests conducted in the spontaneously hypertensive rat (SHR) such as described by I. Vavra, et al., Can. J. Physiol. Pharmacol., 51, 727 (1973), the test method of which is modified so that the test compound is administered orally to the rat by gastric gavage and the systolic blood pressure is measured by the tail-cuff method before administration of the compound and up to 4 hours thereafter. Using this method, the following representative compounds of formula I are effective for reducing the blood pressure (BP) in the spontaneously hypertensive rat (the amount of test compound and its reduction in BP are indicated in the parentheses): 1',2,2-trimethylspiro[cyclopentane-1',3'-[3H]-indol]-2'(1'H)-one (described in Example 1, at a dose of 100 mg/kg of body weight causes a 9% decrease at 90 minutes and a 12% decrease at 4 hours), 4,5-dihydro-1',2,2-trimethylspiro[furan-3(2H),3'(3H)-indol]-2'(1H)-one (described in Example 2, at a dose of 100 mg/kg of body weight causes a 4% decrease at 90 minutes and a 10% decrease at 4 hours), 1'-phenylmethyl-4,5-dihydro-2,2-dimethylspiro[furan-3(2H),3'(3H)-indol]-2'(1'H)-one (described in Example 3, at a dose of 100 mg/kg of body weight causes a 6% decrease at 90 minutes and a 12% decrease at 4 hours) and 1',2',4,5-tetrahydro-1',2-dimethyl-2'-oxospiro[furan-3(2H),3'(3H)-indole]-2-acetic acid (described in Example 4, at a dose of 100 mg/kg of body weight causes a 12% decrease at 90 minutes and a 10% decrease at 4 hours).

The compounds of formula I of this invention are used alone or in combination with pharmacologically acceptable carriers, the proportion of which is determined by the solubility and chemical nature of the compound, chosen route of administration and standard biological practice. For example, they are administered orally in solid form i.e. capsule or tablet. They can also be administered orally in the form of suspensions or solutions or they may be injected parenterally. For parenteral administration they can be used in the form of a sterile solution containing other solutes, for example, enough saline or glucose to make the solution isotonic.

The tablet compositions contain the active ingredient in admixture with non-toxic pharmaceutical excipients known to be suitable in the manufacture of tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula I contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil, for example, arachis oil, olive oil, sesame oil, or coconut oil, in a mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compounds of formula I as antihypertensive agents will vary with the form of administration and the particular compound chosen. Furthermore, it will vary with the particular host as well as the age, weight and condition of the host under treatment as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective antihypertensive amount of the compounds for oral administration usually ranges from about 10 to 500 mg per kilogram body weight per day in single or divided doses although as aforementioned variations will occur. However a dosage level that is in the range of from about 50 to 200 mg per kilogram body weight per day in single or divided doses is employed most desirably for oral administration in order to achieve effective results.

The compound of formula I also can be used to produce beneficial effects in the treatment of hypertension, peripheral and cerebral vascular diseases and related disorders when combined with a therapeutically effective amount of a diuretic and/or antihypertensive agent commonly used in antihypertensive therapy. Such antihypertensive therapeutic agents include, for example, the thiazide diuretics for instance, chlorothiazide or hydrochlorothiazide; mineralo-corticoid antagonizing diuretic agents, e.g., spironolactone; and other diuretics such as triameterene and furosemide. Examples of still other suitable antihypertensive agents are prazosine, hydralazine and centrally active antihypertensive agents such as methyldopa, clonidine, and reserpine; as well as the β-adrenergic blocking agents, for instance, propranolol. In this instance, the compound of formula I can be administered sequentially or simultaneously with the antihypertensive and/or diuretic agent. Preferred antihypertensive therapeutic agents are the antihypertensive agents such as the thiazides, mineralocorticoid antagonizing diuretic agents and the β-adrenergic blocking agents. A combination of the foregoing antihypertensive and/or diuretic agents, e.g. propranolol and hydrochlorothiazide, can be substituted for a single agent. Suitable methods of administration, compositions and dosages of the above described diuretic and/or antihypertensive agents are well known in the art; for instance, "Physician Desk Reference", 32 ed., Medical Economics Co., Oradell, N.J., U.S.A., 1978. For example, the agent propranolol is administered daily to humans in a range of 80 to 640 mg, usually in the form of unit doses of 10, 20, 40 or 80 mg. When used in combination, the compound of formula I is administered as described previously.

PROCESS

The compounds of formula I are prepared by oxidizing a compound of formula II

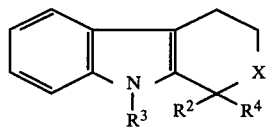
(II)

in which $R^2$ is lower alkyl, $R^3$ is lower alkyl or phenyl(lower)alkyl, $R^4$ is lower alkyl or lower alkoxycarbonyl(lower)alkyl, and X is oxygen or $CH_2$ with sodium periodate to obtain, in the instance wherein $R^4$ of the compound of formula II is lower alkyl, the corresponding compound of formula I

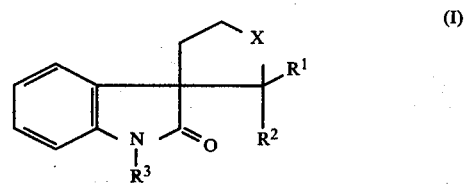
(I)

in which $R^1$ is lower alkyl, and $R^2$, $R^3$ and X are as defined herein, or in the instance wherein $R^4$ of the compound of formula II is lower alkoxycarbonyl(lower)alkyl, the corresponding compound of formula III

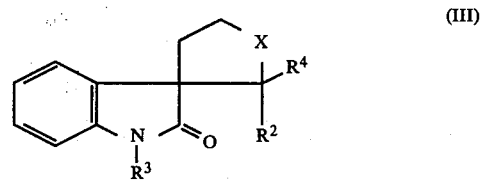
(III)

in which $R^2$, $R^3$ and X are as defined herein and $R^4$ is lower alkoxycarbonyl(lower)alkyl; and followed by alkaline hydrolysis of the compound of formula III to obtain the corresponding compound of formula I in which $R^1$ is carboxy(lower)alkyl, and $R^2$, $R^3$ and X are as defined herein.

The above oxidation with sodium metaperiodate is readily achieved by treating the compound of formula II with two to five molar equivalents of sodium metaperiodate in a solvent of an aqueous water-miscible organic solvent, preferably tetrahydrofuran, dioxane, methanol, ethanol, propanol and the like, at 20° to 100° C. for 15 hours to five days and isolating the corresponding compounds of formula I and III.

The alkaline hydrolysis of the compound of formula III involves the reaction of the compound of formula III with two to ten molar equivalents of potassium or sodium hydroxide in an aqueous lower alkanol, preferably methanol or ethanol, at 60° to 100° C. for 30 to 120 minutes, and isolating the corresponding compound of formula I in which $R^1$ is carboxy(lower)alkyl, and $R^2$, $R^3$ and X are as defined herein.

The starting materials of formula II are either known or can be prepared by known methods, for example, see the reports by B. Robinson and G. F. Smith, J. Chem. Soc., 4574 (1960), L. G. Humber et al., Eur. J. Med. Chem., 10, 215 (1975), C. A. Demerson et al., J. Med. Chem., 18, 189 (1975) and A. A. Asselin et al., U.S. Pat. 4,128,560, issued Dec. 5, 1978.

The following examples illustrate further this invention.

EXAMPLE 1

1',2,2-Trimethylspiro[cyclopentane-1,3'-[3H]-indol]-2'(1'H)-one (I: $R^1$, $R^2$ and $R^3$=Me and X=$CH_2$)

1,2,3,4-Tetrahydro-1,1-dimethylcarbazole[9.4 g, 0.47 mole, described by B. Robinson and G. F. Smith, J. Chem. Soc., 4574 (1960)] in 10 ml of dimethylformamide was added dropwise to stirring 5.2 g of sodium hydride (50% dispersion) in 5 ml of dimethylformamide. After 15 minutes, methyl iodide (12.5 g) was added dropwise and stirring continued for 12 hours. Water was added to destroy excess hydride, diethyl ether was added and the layers were separated. The aqueous phase was extracted with diethyl ether. The ether layers were combined, washed with 10% hydrochloric acid, water, dried and evaporated to afford 10.3 g of crude product. Chromatography on silica gel afforded 7.8 g of 1,2,3,4-tetrahydro-1,1,10-trimethylcarbazole, mp 74°–76° C., and nmr(CDCl$_3$) δ1.46 (6H,s), 2.8 (4H), 2.75 (2H), 3.8 (3H,s) and 7.3 (4H).

The latter compound (6.5 g, 0.0315 mole) was dissolved in 130 ml of methanol. Sodium metaperiodate (20 g) in 90 ml of water was added dropwise with stirring. After stirring at room temperature overnight, the precipitate was filtered off and filtrate was evaporated. The residue was taken into benzene, washed with water, dried and evaporated to give 7.3 g of crude product. This was chromatographed on silica gel using benzene to give a purified residue (2.2 g) which was crystallized from petroleum ether to give the title compound: mp 99°–101° C., and Anal. Calcd for $C_{15}H_{19}NO$: C, 78.56% H, 8.35% N, 6.11% and Found: C, 78.71% H, 8.36% N, 5.88%.

EXAMPLE 2

4,5-Dihydro-1′,2,2-trimethylspiro[furan-3(2H), 3′(3H)-indol]-2′(1′H)-one (I: $R^1$, $R^2$ and $R^3$=Me and X=O)

A solution of 1,3,4,9-tetrahydro-1,1-dimethylpyrano[3,4-b]indole [10 g, 0.0498 mole, described by C. A. Demerson et al., J. Med. Chem., 18, 189 (1975)] in 25 ml of dry dimethylformamide was added dropwise to a stirring suspension of 6 g of 55% sodium hydride in 25 ml of dimethylformamide while cooling. The mixture was stirred for one hour at 40° C., and 5 ml of iodomethane was added. The mixture was stirred at 40° C. overnight and poured into ice-water. The resulting mixture was neutralized with aqueous hydrochloric acid, extracted with diethyl ether, washed with water, dried and evaporated to give 15 g of an oil. A solution of this oil was treated with charcoal, and the filtrate was evaporated and crystallized from hexane to give 8.5 g of 1,3,4,9-tetrahydro-1,1,9-trimethylpyrano[3,4-b]indole, mp 96°–97° C.

A solution of the latter compound (8.3 g, 0.0386 mole) in 150 ml of methanol was added dropwise to 17 g of sodium periodate in 75 ml of water. This was stirred at room temperature for twenty four hours and filtered, and the filtrate was concentrated. Water was added and the solution was extracted with chloroform. The extract was washed with water, dried and evaporated to give 8.4 g of a brown oil. Chromatography on silica gel with 10% acetone in benzene gave 7.0 g of a pure yellowish oil that partially crystallized. Recrystallization from petroleum ether gave the title compound, mp 54°–57° C., and Anal. Calcd for $C_{14}H_{17}NO_2$: C, 72.70% H, 7.41% N, 6.06% and Found: C, 72.41% H, 7.40% N, 6.15%.

EXAMPLE 3

1′-Phenylmethyl-4,5-dihydro-2,2-dimethylspiro[furan-3(2H),3′(3H)-indol]-2′(1′H)-one (I: $R^1$ and $R^2$=Me, $R^3$=phenylmethyl and X=O)

1,3,4,9-Tetrahydro-1,1-dimethylpyrano[3,4-b]indole (5 g, 25 mmole, described by C. A. Demerson et al., cited above) was added portionwise to a suspension of sodium hydride (3 g, 58% dispersion in mineral oil) in 25 ml of dry dimethylformamide. This was stirred at room temperature for one hour. Benzyl chloride (3.8 g, 30 mmole) was added dropwise with ice cooling. The temperature was raised to 40° C. for 30 min. The reaction was poured into ice-water and the mixture was extracted with diethyl ether, washed twice with water, dried and evaporated. The solid residue (10 g) was chromatographed on silica gel using 10% ethyl acetate in benzene to afford 4.5 of white solid which was crystallized from butanol to give 9-phenylmethyl-1,3,4,9-tetrahydro-1,1-dimethylpyrano[3,4-b]indole, mp 132°–134° C.

The latter compound (19 g) in 600 ml of tetrahydrofuran was slowly added to 39.4 g of sodium periodate in 120 ml of water and the mixture was refluxed for 3 days. Most of the tetrahydrofuran was evaporated, water was added and the mixture was extracted with chloroform. The combined chloroform extracts were washed twice with water, dried and evaporated to give 22 g of oil. This was chromatographed on silica gel using 10% ethyl acetate in benzene to afford 14.4 g of solid product which was crystallized from ethanol to give the title compound mp 101°–103° C., and Anal. Calcd for $C_{20}H_{21}NO_2$: C, 78.14% H, 6.89% N, 4.56% and Found C, 78.12% H, 6.87% N, 4.82%.

EXAMPLE 4

1′,2′,4,5-Tetrahydro-1′,2-dimethyl-2′-oxospiro[furan-3(2H),3′(3H)-indole]-2-acetic Acid (I: $R^1$=carboxymethyl, $R^2$ and $R^3$=Me and X=O)

A solution of 1,3,4,9-tetrahydro-1,9-dimethylpyrano[3,4-b]indole-1-acetic acid (12 g, described by C. A. Demerson et al., cited above) in 100 ml of anhydrous ethanol containing 10 ml of concentrated sulfuric acid was allowed to remain at room temperature for two days. This was diluted with water and extracted with chloroform. The extract was washed with 5% sodium bicarbonate and water, dried and evaporated to afford 11 g of dark brown oil. Chromatography on silica gel using 30% ethyl acetate in benzene afforded 7 g of 1,3,4,9-tetrahydro-1,9-dimethylpyrano[3,4-b]indole-1-acetic acid ethyl ester, nmr(CDCl$_3$) δ1.65 (d, 3H), 1.75 (s, 3H), 3.85 (m, 2H), 3.9–4.3 (m, 2H), 4.1 (q, 2H) and 3.75 (s, 3H).

A solution of the latter ester (7.0 g) in 150 ml of ethanol was added to 14 g of sodium periodate in 30 ml of ethanol. This was refluxed for 3 days and filtered. The filtrate was concentrated and water was added. The solution was extracted with chloroform and the extract was washed with water, dried and evaporated to afford an oil (7.0 g) of 1′,2′,4,5-tetrahydro-1,2-dimethyl-2′-oxospiro[furan-3(2H),3′(3H)-indole]-2-acetic acid ethyl ester.

The latter compound (7.0 g) was dissolved in 200 ml of methanol and 7 g of potassium hydroxide in 30 ml of water was added and the solution was refluxed for one hour. Most of the methanol was evaporated, and water was added. The solution was washed with benzene, made acidic with 20% hydrochloric acid and extracted with benzene. The organic extract was dried and evaporated to give 4 g of yellow foam. Crystallization from benzene gave 2.5 g of the title compound, mp 149°–151° C., and Anal. Calcd for $C_{15}H_{17}NO_4$: C, 65.44% H, 6.22% N, 5.09% and Found: C, 65.76% H, 6.25% N, 5.14%.

We claim:

1. A compound of formula I

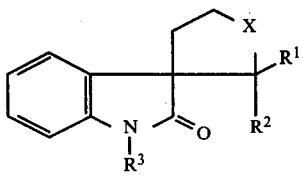

in which $R^1$ is lower alkyl or carboxy(lower)alkyl, $R^2$ is lower alkyl, $R^3$ is lower alkyl or phenyl(lower)alkyl, and X is oxygen or $CH_2$, or a therapeutically acceptable base addition salt thereof when $R^1$ is carboxy(lower)alkyl.

2. A compound of claim 1 in which $R^1$ is lower alkyl or carboxymethyl, $R^2$ is lower alkyl, and $R^3$ is lower alkyl or phenylmethyl, or a therapeutically acceptable base addition salt thereof when $R^1$ is carboxymethyl.

3. 1',2,2-Trimethylspiro[cyclopentane-1,3'[3H]indol]-2'(1'H)-one, a compound of claim 1 wherein $R^1$, $R^2$ and $R^3$ are methyl and X is $CH_2$.

4. 4,5-Dihydro-1',2,2-trimethylspiro[furan-3(2H),3'(3H)-indol]-2'(1'H)-one, a compound of claim 1 wherein $R^1$, $R^2$ and $R^3$ are methyl and X is oxygen.

5. 1'-Phenylmethyl-4,5-dihydro-2,2-dimethylspiro[furan-3(2H),3'(3H)-indol]-2'(1'H)-one, a compound of claim 1 wherein $R^1$, $R^2$ are methyl, $R^3$ is phenylmethyl and X is oxygen.

6. 1',2',4,5-Tetrahydro-1',2-dimethyl2'-oxospiro[furan-3(2H),3'(3H)-indole]-2-acetic acid, a compound of claim 1 wherein $R^1$ is carboxymethyl, $R^2$ and $R^3$ are methyl and X is oxygen.

7. A pharmaceutical composition for treating hypertension, which comprises an effective amount of a compound of claim 1, and a pharmaceutically acceptable carrier therefor.

8. A method of treating hypertension in a hypertensive mammal, which comprises administering to said mammal an effective antihypertensive amount of a compound of claim 1.

9. A method of treating hypertension in a hypertensive mammal, which comprises administering to the mammal an antihypertensive effective amount of a compound of claim 1, in combination with an effective amount of a diuretic, or an antihypertensive agent or a combination of a diuretic and an antihypertensive agent.

10. The method of claim 9 in which the agent is a diuretic thiazide, a mineralocorticoid antagonizing diuretic agent or a β-adrenergic blocking agent.

11. The method of claim 9 in which the agent is chlorothiazide, hydrochlorothiazide or propranolol.

12. The method of claim 9 in which the compound of formula I, and the diuretic and/or antihypertensive agent is administered sequentially or simultaneously.

13. A pharmaceutical composition for treating hypertension comprising an effective amount of a compound of claim 1, and a diuretic or antihypertensive agent.

14. The pharmaceutical composition of claim 13 in which the agent is a diuretic thiazide, a mineralocorticoid antagonizing diuretic agent or a β-adrenergic blocking agent.

15. The pharmaceutical composition of claim 13 in which the agent is chlorothiazide, hydrochlorothiazide or propranolol.

16. A process for preparing a compound of formula I

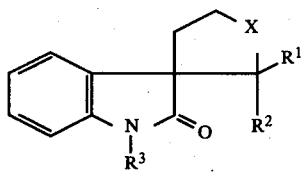

in which $R^1$ is lower alkyl or carboxy(lower)alkyl, $R^2$ is lower alkyl, $R^3$ is lower alkyl or phenyl(lower)alkyl, and X is oxygen or $CH_2$, which comprises oxidizing a compound of formula II

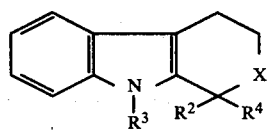

in which $R^2$, $R^3$ and X are as defined herein and $R^4$ is lower alkyl or lower alkoxycarbonyl(lower)alkyl with sodium periodate to obtain, in the instance wherein $R^4$ of the compound of formula II is lower alkyl, the corresponding compound of formula I in which $R^1$ is lower alkyl, and $R^2$, $R^3$ and X are as defined herein, or in the instance wherein $R^4$ of the compound of formula II is lower alkoxycarbonyl(lower)alkyl, the corresponding compound of formula III

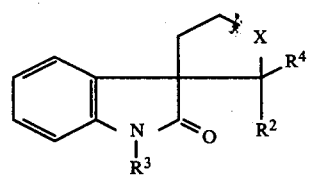

in which $R^2$, $R^3$ and X are as defined herein and $R^4$ is lower alkoxycarbonyl(lower)alkyl, and hydrolyzing said compound of formula III under alkaline conditions to obtain the corresponding compound of formula I in which $R^1$ is carboxy(lower)alkyl, and $R^2$, $R^3$ and X are as defined herein.

* * * * *